United States Patent
Anapliotis

(10) Patent No.: US 10,603,057 B2
(45) Date of Patent: Mar. 31, 2020

(54) STERILIZABLE DISPOSABLE SURGICAL INSTRUMENT FOR BONE FUSION SURGERY

(71) Applicant: Merete Holding GmbH, Berlin (DE)

(72) Inventor: Emmanuel Anapliotis, Berlin (DE)

(73) Assignee: Merete Holding GmbH, Berlin (DE)

( * ) Notice: Subject to any disclaimer, the term of this patent is extended or adjusted under 35 U.S.C. 154(b) by 83 days.

(21) Appl. No.: 15/761,619

(22) PCT Filed: Oct. 12, 2016

(86) PCT No.: PCT/DE2016/000371
§ 371 (c)(1),
(2) Date: Mar. 20, 2018

(87) PCT Pub. No.: WO2017/067532
PCT Pub. Date: Apr. 27, 2017

(65) Prior Publication Data
US 2018/0344336 A1    Dec. 6, 2018

(30) Foreign Application Priority Data
Oct. 19, 2015 (DE) .......................... 10 2015 013 613

(51) Int. Cl.
*A61B 17/17*    (2006.01)
*A61B 17/72*    (2006.01)
(Continued)

(52) U.S. Cl.
CPC ...... *A61B 17/1775* (2016.11); *A61B 17/1633* (2013.01); *A61B 17/1682* (2013.01);
(Continued)

(58) Field of Classification Search
CPC .................. A61B 17/7291; A61B 17/1775
See application file for complete search history.

(56) References Cited

U.S. PATENT DOCUMENTS

2010/0131072 A1\* 5/2010 Schulte .................. A61B 17/68
623/21.11
2013/0066383 A1 3/2013 Anderson et al.
(Continued)

FOREIGN PATENT DOCUMENTS

DE    102009052119    5/2011

OTHER PUBLICATIONS

Merete FootFamily, Merete Foot & Ankle Solutions, published Nov. 2017, 1 pg.
(Continued)

*Primary Examiner* — Olivia C Chang
(74) *Attorney, Agent, or Firm* — Andrus Intellectual Property Law, LLP

(57) ABSTRACT

A sterilizable disposable surgical instrument is formed by an implant for bone fusion as well as an implant sleeve surrounding the implant for bone fusion. The implant has a distal implant section, a proximal implant section, and a coupling section with a polygonal cross-section profile between the distal and proximal implant section. The implant sleeve has a protective cap and a handle, which can be connected to one another. A first bore is configured in the protective cap in the longitudinal direction and receives the proximal implant section of the implant. A second bore is configured in the handle running in the longitudinal direction and receives the distal implant section of the implant for bone fusion. A coupling region having a through-opening is configured in the second bore in the handle, into which the coupling section of the implant for bone fusion engages in an integral and force-locking manner.

9 Claims, 3 Drawing Sheets

Figure 1:
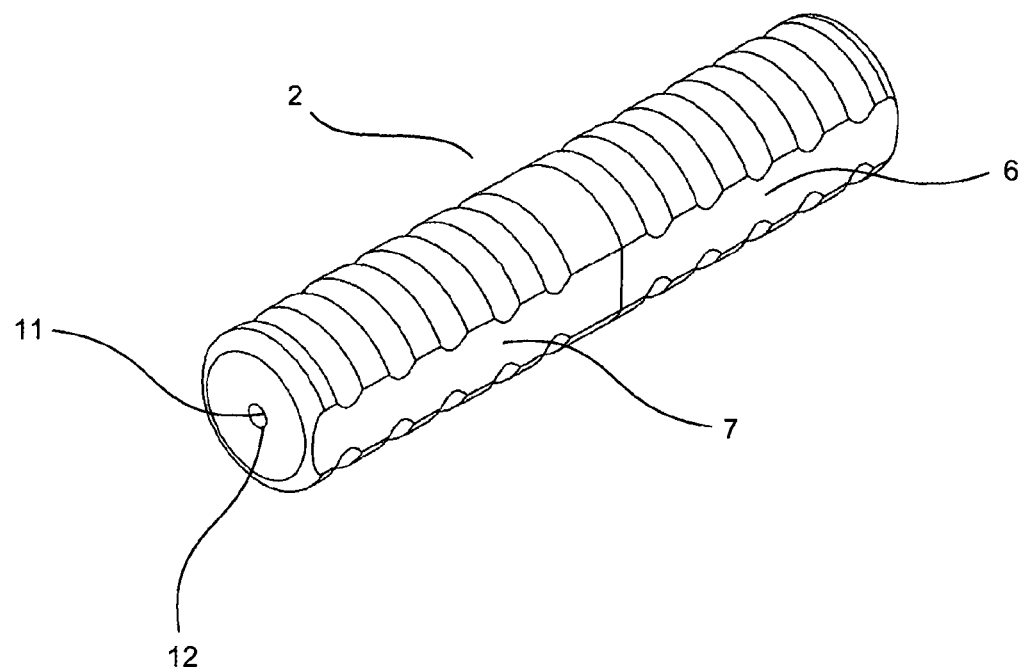

(51) Int. Cl.
| | |
|---|---|
| *A61F 2/46* | (2006.01) |
| *A61B 17/86* | (2006.01) |
| *A61B 17/88* | (2006.01) |
| *A61B 17/68* | (2006.01) |
| *A61B 17/16* | (2006.01) |
| *A61B 17/00* | (2006.01) |
| *A61B 17/92* | (2006.01) |

(52) U.S. Cl.
CPC ........ *A61B 17/685* (2013.01); *A61B 17/7291* (2013.01); *A61B 17/862* (2013.01); *A61B 17/863* (2013.01); *A61B 17/8883* (2013.01); *A61B 17/8891* (2013.01); *A61F 2/4606* (2013.01); *A61B 17/7233* (2013.01); *A61B 17/8875* (2013.01); *A61B 17/92* (2013.01); *A61B 2017/00004* (2013.01); *A61B 2017/0023* (2013.01)

(56) References Cited

U.S. PATENT DOCUMENTS

| | | |
|---|---|---|
| 2013/0123862 A1 | 5/2013 | Anderson et al. |
| 2013/0274814 A1 | 10/2013 | Weiner et al. |
| 2014/0277186 A1 | 9/2014 | Granberry et al. |

OTHER PUBLICATIONS

Merete FootFamily, Fubchirurgie Katalog 2016, publsihed Jun. 2016, 2 pgs.
Merete MetaToe ReadyToUse Kit, Absorbable Implants for PIP and DIP arthrodesis in innovative sterial packaging, published May 2018, 2 pgs.
Merete MetaToe ReadyToUse Kit, Resorbierbares Implantat fur die PIP- und DIP-Arthrodese in Innovatoiver Sterilverpackung, published Apr. 2018, 2 pgs.
Merete MetaToe ReadyToUse Kit, Absorbable Implants for PIP and DIP arthrodesis in innovative sterile packaging, MetaToe EndoSorb, now in sterile Merete miniPack, published Apr. 2016, 2 pgs.
International Search Report, PCT/DE2016/000371, dated Feb. 13, 2017.
Written Opinion, PCT/DE2016/000371, dated Apr. 27, 2017.
Merete: "Meta Toe (TM) ReadyToUse Kit," Apr. 30, 2016 (Apr. 30, 2016), XP055341424, Berlin Found on the Internet: URL:http://www.merete-medical.com/de/images/stories/Publikationen/flyer_metatoe_rtu_screen.pdf, found on Feb. 2, 2017.
Merete et al: "merete & friends sterile angle stability and innovative osteotomy technology," Jan. 31, 2016 (Jan. 31, 2016), XP055341494, Found on the Internet: URL:http://www.merete-medical.com/de/images/stories/newsletter/merete_and_friends_rz_screen.pdf, found on Feb. 2, 2017.

* cited by examiner

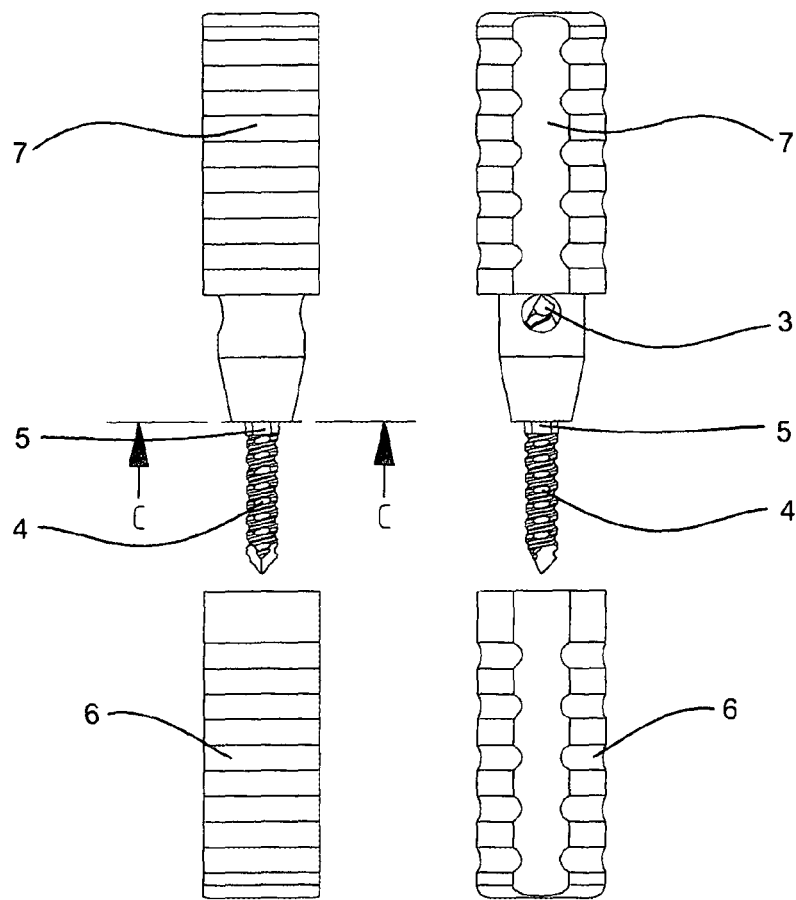
Fig. 3.1    Fig. 3.2
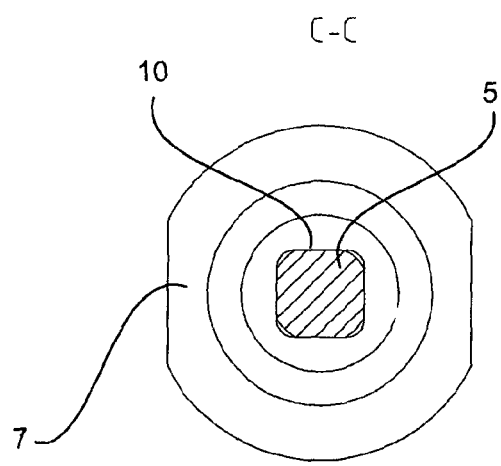
Fig. 3.3

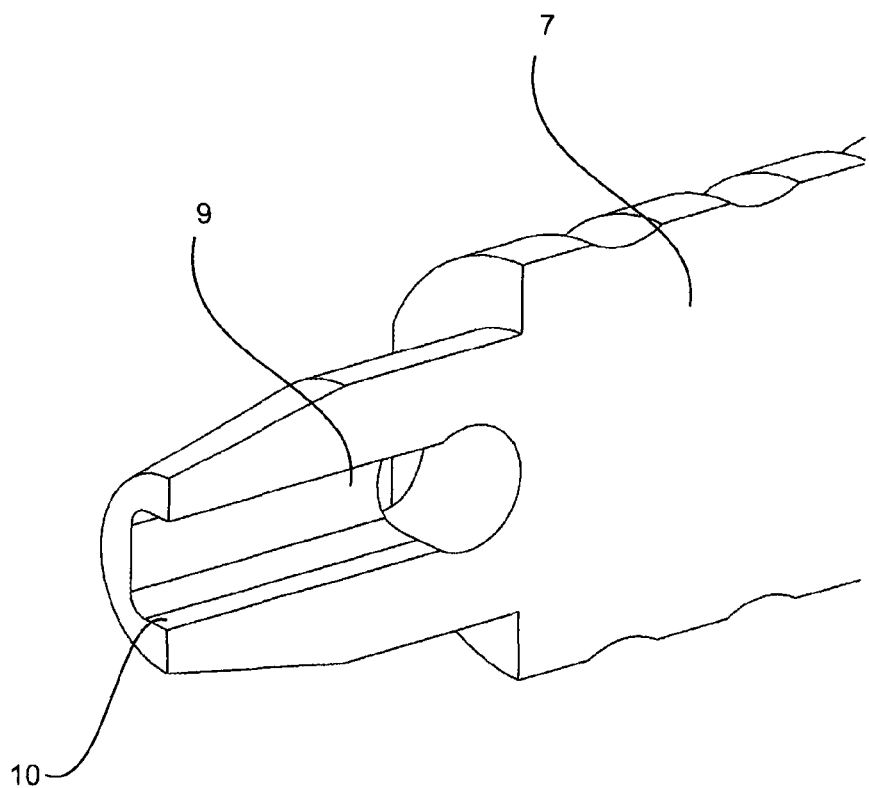
Fig. 4.1
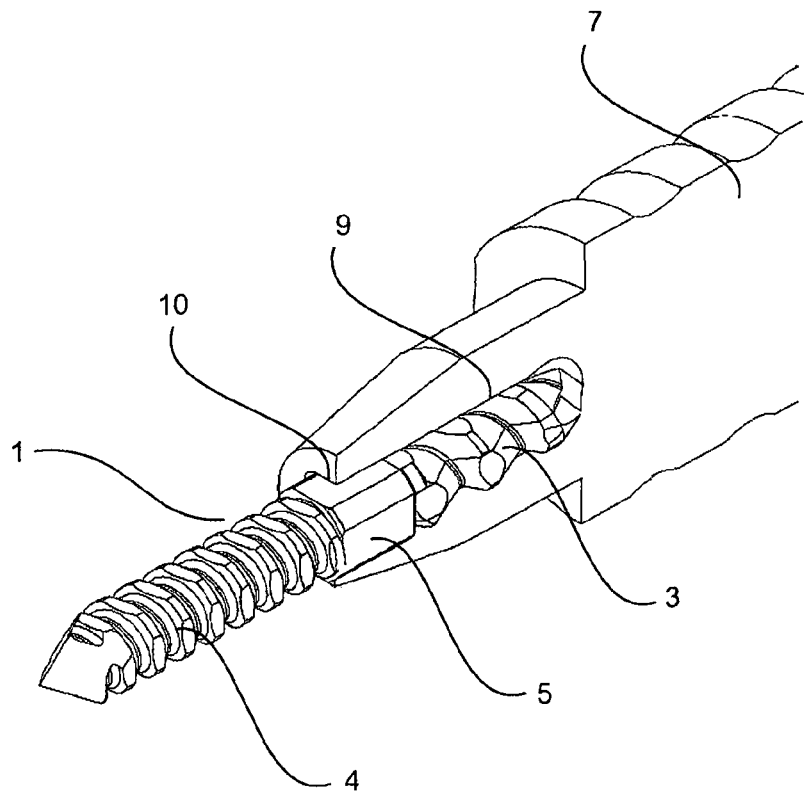
Fig. 4.2

STERILIZABLE DISPOSABLE SURGICAL INSTRUMENT FOR BONE FUSION SURGERY

CROSS-REFERENCE TO RELATED APPLICATIONS

This application is the U.S. national stage application of International Application PCT/DE2016/000371, filed Oct. 12, 2016, which international application was published on Apr. 27, 2017, as International Publication WO 2017/067532. The International Application claims priority of German Patent Application No. 10 2015 013 613.5, filed Oct. 19, 2015. The international application and German application are both incorporated herein by reference, in entirety.

The invention relates to a sterilizable surgical single-use instrument, as well as to a sterile-packed instrument set for bone fusion surgery, in particular for interphalangeal arthrodesis for correction of a hammer toe, comprising an implant for bone fusion as well as a holder handle for the bone fusion implant.

Formation of a hammer toe is one of the most frequent incorrect positions of toes; it manifests itself by hyperextension of the metatarsophalangeal joint with simultaneous flexion of the interphalangeal joint. As a result, the toe is bent downward similar to a hammer, and this leads to painful symptoms such as corns or, going even further, to inflammatory states in the toe joints.

For correction of a hammer toe, the bent joint is opened up and subsequently, one or both of the joint heads is/are removed. Straightening and reinforcement of the joint generally takes place by means of a wire or by way of a bone fusion implant, with which the joint surfaces are connected with one another.

One operation technique provides that a bore is placed into the proximal joint surface for introduction of the bone fusion implant, into which bore the proximal implant section of a bone fusion implant is screwed. To bring the two joint surfaces together, a second bore is placed into the distal joint surface, which bore then accommodates the distal implant section of the bone fusion implant, and thereby the joint surfaces are pressed against one another.

Instruments for introducing bone fusion implants into a bone are known from the state of the art.

For example, US 2014/0277186 A1 discloses a surgical instrument for interphalangeal arthrodesis, having an interchangeable handle for the bone drill and for the screwdriver used to fix the bone fusion implant in place in the bone.

A set of bone fusion instruments for correction of a hammer toe is described in US 2013/0274814 A1, which set comprises a socket wrench for introducing a two-part hammer-toe implant into the toe bone. The socket wrench consists of a handle and of a tool shaft that can be inserted into the handle. A socket is arranged at the proximal end of the tool shaft, in which socket either the male or the female implant component is held, in each instance, mounted at the connection end.

It is a disadvantage of the known instrument sets for implanting bone fusion implants that they are configured as reusable instruments and must be cleaned, packaged, and sterilized again after every operation.

Such instruments are cost-intensive in terms of their production and procurement, so that in general, they are not kept on hand in large amounts by hospitals or physicians. This leads to the result that only a limited number of instrument sets is available to a surgeon for performing multiple similar operations. This restricts the number of operations that can be carried out by a physician, one after the other, to the number of sterile instrument sets that are available. Otherwise, the time expended by the physician increases due to waiting times caused by the required intermediate cleaning and sterilization of the surgical instruments.

It is therefore a task to indicate an instrument for introduction of bone fusion implants, in particular an instrument for interphalangeal arthrodesis, which instrument can be produced in a price-advantageous manner and can also be stored in a sterile manner over a long period of time, and therefore can be kept on hand.

To accomplish this task, a sterilizable surgical single-use instrument is indicated, consisting of an implant for bone fusion and an implant sleeve that encloses the implant for bone fusion. The implant for bone fusion has a distal implant section, a proximal implant section, and a coupling section situated between the distal and the proximal implant section and having a polygonal cross-sectional profile.

The implant sleeve consists of a protective cap and a handle part, which are configured so that they can be connected with one another. Preferably, the protective cap can be set onto or screwed onto the handle part.

A first bore that runs in the longitudinal direction is arranged in the protective cap; this bore is prepared for accommodating the proximal implant section of the implant for bone fusion. The proximal implant section is introduced into the first bore through a first opening arranged at the distal face side of the protective cap, and is circumferentially enclosed by the inner wall of the first bore, over its full area, in the introduced state.

A bore that also runs in the longitudinal direction is arranged in the handle part, which bore will be referred to as the "second bore" hereinafter, and is prepared for accommodating the distal implant section of the implant for bone fusion. The distal implant section is introduced into the second bore through an opening arranged on the distal face side of the handle part, and is circumferentially enclosed by the inner wall of the second bore, over its full area, after having been introduced into it.

The single-use instrument according to the invention is characterized in that a coupling region having a polygonal passage opening is arranged in the second bore in the handle part, into which bore the coupling section of the implant for bone fusion engages with shape fit and/or force fit.

As a result, the invention describes a single-use instrument for bone fusion surgery, in which a bone fusion implant is releasably inserted in the handle part of an implant sleeve and completely enclosed by the implant sleeve when the protective cap is set onto the handle part. The handle part of the implant sleeve is prepared for inserting the bone fusion implant into a bone, preferably by means of pressing down on or rotating the handle part.

The term "single-use instrument" refers to a surgical instrument in the form of a disposable part, which is not cleaned, packaged, and sterilized for renewed use after having been used once, but rather is disposed of directly.

The implant for bone fusion according to the invention, also referred to as a bone fusion implant in this context, is preferably configured in one piece and essentially consists of three sections that make a transition into one another, namely a proximal region, a distal region, and a center region having a coupling section. In particular, the implant for bone fusion according to the invention is an implant for use in PIP or DIP arthrodesis, preferably a hammer-toe implant.

For implantation, the bone fusion implant is screwed into the bone with its proximal implant section by turning the handle part and/or pressed into the bone by pressing down on the handle.

The proximal implant section is, in particular, a proximal implant screw thread, which is screwed into the bone, preferably into the medullary canal of the bone, i.e., in an intramedullary manner, proceeding from the distal joint surface.

Furthermore, the proximal implant section can have any other profile prepared for fixation in a bone bore. Such profile shapes are, in particular, grooved profiles or lamellar profiles, or also profiles having hook-shaped projections. Also, the proximal implant section can have one or more longitudinal incisions that run in the longitudinal direction.

The distal implant section is, in particular, a distal implant screw thread that is prepared for being introduced into the bone, i.e., its medullary canal, proceeding from the distal joint surface. In general, this implant section is pressed into or pushed into a prepared bone bore.

Alternatively, however, the distal implant section can also have any other profile prepared for fixation in a bone bore, such as preferably, grooved profiles or lamellar profiles, or also profiles having hook-shaped projections. Also, the distal implant section can have one or more longitudinal incisions that run in the longitudinal direction.

The coupling section, having a polygonal cross-sectional profile, lies between the proximal and the distal implant section and essentially forms a center region of the implant. The term polygonal cross-sectional profile refers to a profile that is preferably configured as an equilateral polygon, in particular with four, six or eight corners.

The coupling region arranged in the second bore in the handle part, having a continuous passage opening, is preferably configured as an equilateral polygon, in particular with four, six or eight corners. It is advantageous if the coupling region is arranged in the region of the second opening situated on the face side. The cross-sectional profile of the coupling section (implant) is configured with matching fit and shape fit with the passage opening of the coupling region (handle part). In this regard, the wall of the passage opening encloses the coupling section in a radially circumferential manner, so that the coupling section is surrounded by the wall of the passage opening in the coupling region over its full circumference.

It is characteristic for the structure of the bone fusion implant that its coupling section has a greater outside diameter than the distal implant section, so that the distal implant section can be pushed through the passage opening into the second bore in the handle part.

The implant for bone fusion is inserted into the implant sleeve before sterilization of the single-use instrument. For this purpose, the bone fusion implant is pushed into the second bore in the handle part of the implant sleeve with its distal implant section, to such an extent that the coupling section of the bone fusion implant engages into the coupling region of the second bore with shape fit. The proximal implant section projects out of the handle part after the bone fusion implant has been inserted.

The coupling region of the handle part and the coupling section of the bone fusion implant are configured in such a manner, in terms of their matching shape, that these form a force fit during implantation of the bone fusion into the bone, which allows transfer of force from the handle part to the bone fusion implant. Fixation of the distal implant section in the handle part takes place exclusively on the basis of the matching fit of the passage opening and the coupling section.

The bores in the protective cap and in the handle part of the implant sleeve are disposed in such a manner that when the protective cap and the handle part are connected, the first opening of the first bone makes a flush connection with the second opening of the second bore, so that when the implant sleeve is closed, a cavity having a closed wall is formed, in which the bone fusion implant is enclosed.

In a particular embodiment, the length of the second bore in the handle part is less than or equal to the summary length of the coupling section and the distal implant section of the implant for bone fusion. In this embodiment, the end region of the distal implant section makes contact with the bottom wall of the second bore, so that pressure in the direction of the proximal bone can be exerted on the bone fusion implant in its longitudinal direction in order to screw the bone fusion implant in.

In one embodiment, the second bore in the handle is configured as a dead-end bore, with its end that lies opposite the second opening preferably being configured in a closed manner. In an alternative embodiment to this, the second bore in the handle part makes a transition, in the axial direction, into a linear passage bore having an inside diameter that is smaller than the smallest outside diameter of the distal implant section, with the passage bore ending in an opening in the bottom of the handle part.

This passage bore is prepared, in particular, for guiding an auxiliary instrument for releasing the bone fusion implant from its shape-fit coupling with the handle part within the bore, so as to be able to gently press the bone fusion implant out of the second bore. It is advantageous if the auxiliary instrument is a rod produced from surgical metal or plastic, which rod is introduced into the second bore in the handle part from the outside, through the passage bore.

In an advantageous embodiment, the implant for bone fusion consists of a bioresorbable or biodegradable material, in particular PLGA, of a biocompatible plastic, preferably PEEK, or of titanium.

It is advantageous if the handle part and the protective cap of the implant sleeve are produced from a plastic for medical products.

For rapid and easy recognition of which section of the implant sleeve is the handle part and which section is the protective cap, the handle part and the protective cap of the implant sleeve can be configured so as to be distinguished from one another optically and/or haptically. In a configuration using means that can be optically differentiated, the protective cap and the handle part can have different colors. In the case of differentiability using haptic means, the protective cap and the handle part can have surface structures that are different from one another.

In a preferred embodiment, the handle part has a maximal length of 30 mm-40 mm between its proximal face side, on which the second opening of the second bore is arranged, and its distal end. The maximal outside diameter lies between 5 mm-30 mm, preferably between 7 mm-15 mm. When using the single-use instrument according to the invention, significantly lower lever forces and torsion forces are exerted on the bone fusion implant to be implanted by means of this miniaturized embodiment, in which the handle part can be guided only between the fingers of the surgeon due to its low length, as compared with conventional, longer surgical screw-in instruments, and thereby the risk of implant fractures due to the mechanical action by the surgeon is clearly reduced. This is significantly advantageous, in particular, in the implantation of bone fusion implants composed of resorbable or biodegradable materials, which are more brittle and more liable to break than non-degradable plastics or metals.

Furthermore, the invention comprises a sterile-packed instrument set for single use, containing a surgical single-use instrument according to one of the aforementioned embodiments, in which the sterile packaging consists at least of a sterile barrier system and a protective packaging. Such sterile packagings allow sterile storage in inventory for up to several years.

Preferably, the sterile-packed instrument set additionally comprises a bone drill for preparation of the bone holes in the bone. Furthermore, the instrument set can comprise an auxiliary instrument for releasing the bone fusion implant for bone fusion from its shape-fit coupling with the handle part. Such an auxiliary instrument can be a plunger, a rod, or a pusher, for example.

Figure 2:
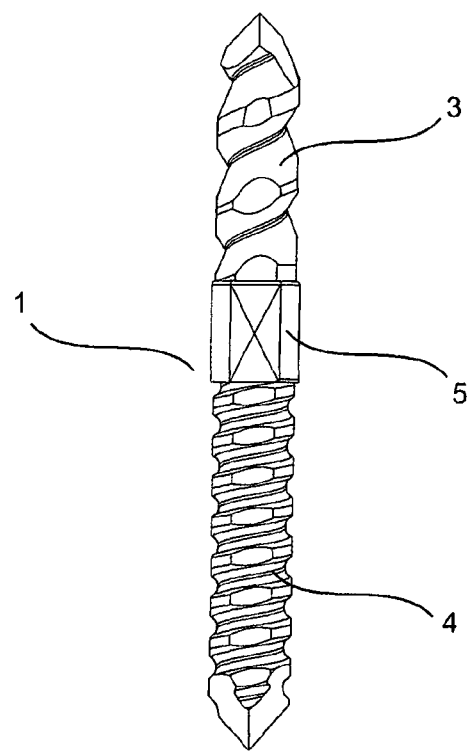

In the following, the invention will be explained in greater detail using an exemplary embodiment. The figures show:

FIG. 1: implant sleeve;
FIG. 2: implant for bone fusion;
FIGS. 3.1-3.3: single-use instrument with opened implant sleeve and inserted bone fusion implant, and
FIGS. 4.1 and 4.2: longitudinal section through the single-use instrument.

FIG. 1 shows the sterilizable surgical single-use instrument in the closed state. The handle part 7 and the protective cap 6 of the implant sleeve 2 are set onto one another with matching fit. An opening 12 is arranged in the bottom of the handle part 7, which opening makes a transition into the linear passage bore 11. A rod-shaped auxiliary instrument can be introduced into the opening 12 in order to push the bone fusion implant out of the second bore in the handle part 7.

FIG. 2 shows an exemplary embodiment of a hammer-toe implant 1 having a proximal threaded section 4, a distal threaded section 3, as well as a coupling section 5 having a polygonal cross-sectional profile.

In FIGS. 3.1 to 3.3, the sterilizable surgical single-use instrument is shown in the opened state. The hammer-toe implant 1 is inserted into the handle part 7 with its distal threaded section 3, with the coupling section 5 engaging into the square passage opening of the coupling region 10 with shape fit, with its essentially square cross-sectional profile, and interacting with this opening with force fit.

The handle part 7 and also the protective cap 6 are equipped with handling grooves that run radially, and allow slip-free rotation between the fingers. In the longitudinal direction, both the handle part 7 and the protective cap 6 have flat surfaces, which on the one hand prevent the single-use instrument from rolling away on a smooth surface, and also improve the exertion of force by the surgeon on the single-use instrument, for example when screwing the bone fusion implant 1 into the proximal bone.

The proximal region of the handle part 7 has a lesser outside diameter than the distal region of the handle part 7, and furthermore conically converges toward the proximal end. The protective cap 6 for closing the implant sleeve 2 is set onto this region, so as to cover the proximal implant section 4.

The protective cap 6 is configured to be longer than the proximal threaded section 4 of the bone fusion implant 1 that projects out of the handle part 7, so that the protective cap 6 completely encloses the proximal threaded section 4 when the implant sleeve 2 is closed by setting the protective cap 6 onto the handle part 7.

FIGS. 4.1 and 4.2 show the handle part 7 of the single-use instrument according to the invention in a longitudinal section. The second bore 9, which is configured as a dead-end bore, and the coupling region 10, having a square passage opening, are shown.

The distal threaded section 3 of the bone fusion implant 1 is pushed into the dead-end bore 9 until it makes contact with the end of the bore hole. The coupling section 5, having an octagonal cross-sectional profile, engages into the square passage opening of the coupling region 10 essentially with shape fit. The proximal threaded section 4 of the bone fusion implant 1 projects completely out of the handle part 7.

REFERENCE SYMBOLS 1) implant for bone fusion
2) implant sleeve
3) distal implant section
4) proximal implant section
5) coupling section having a polygonal cross-sectional profile
6) protective cap
7) handle part
8) first bore for accommodating the proximal threaded region of the bone fusion implant
9) second bore for accommodating the distal threaded region of the bone fusion implant
10) coupling region having a polygonal passage opening in the handle part
11) linear passage bore in the handle part
12) opening in the bottom of the handle part

The invention claimed is:

1. A sterilizable surgical single-use instrument comprising:
an implant for bone fusion, as well as an implant sleeve that completely encloses the implant for bone fusion,
wherein the implant for bone fusion has a distal implant section, a proximal implant section, and a coupling section situated between the distal and proximal implant sections, having a polygonal cross-sectional profile,
wherein the implant sleeve has a protective cap and a handle part, which are configured so as to be connected with one another,
wherein a first bore that runs in a longitudinal direction is arranged in the protective cap, which first bore is prepared for accommodating the proximal implant section of the implant for bone fusion, wherein a second bore that runs in the longitudinal direction is arranged in the handle part, which second bore is prepared for accommodating the distal implant section of the implant for bone fusion,
wherein a coupling region having a passage opening having a polygonal cross-sectional profile is arranged in the second bore in the handle part, into which passage opening the coupling section of the implant for bone fusion engages with shape fit and force fit.

2. The sterilizable surgical single-use instrument according to claim 1, wherein the second bore in the handle part is a dead-end bore.

3. The sterilizable surgical single-use instrument according to claim 1, wherein the second bore in the handle part makes a transition, in an axial direction, into a linear passage bore having an inside diameter that is smaller than the smallest outside diameter of the distal implant section, wherein the passage bore ends in an opening in the bottom of the handle part.

4. The sterilizable surgical single-use instrument according to claim 1, wherein the implant for bone fusion is made of a bioresorbable material of a biocompatible plastic or of titanium.

5. The sterilizable surgical single-use instrument according to claim 1, wherein the implant sleeve is entirely produced from a plastic for medical products.

6. The sterilizable surgical single-use instrument according to claim 1, wherein the handle part and the protective cap of the implant sleeve are configured so as to be distinguished from one another at least one of optically and haptically.

7. The sterilizable surgical single-use instrument according to claim 1, wherein the length of the second bore has a length in the handle part that is less than or equal to a summary length of the coupling section and the distal implant section of the implant for bone fusion.

8. The sterilizable surgical single-use instrument according to claim 1, wherein the handle part has a maximal length of 30 mm-40 mm and a maximal outside diameter of 5 mm-30 mm.

9. The sterilizable surgical single-use instrument according to claim 1, wherein the sterilizable surgical single-use instrument comprises an auxiliary instrument for releasing the implant for bone fusion from shape-fit coupling with the handle part.

* * * * *